(12) United States Patent
Itoh et al.

(10) Patent No.: US 8,587,844 B2
(45) Date of Patent: Nov. 19, 2013

(54) IMAGE INSPECTING APPARATUS, IMAGE INSPECTING METHOD, AND IMAGE FORMING APPARATUS

(75) Inventors: Hitoshi Itoh, Kanagawa (JP); Fumihiro Nakashige, Kanagawa (JP); Keiji Kojima, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 148 days.

(21) Appl. No.: 13/067,382

(22) Filed: May 27, 2011

(65) Prior Publication Data

US 2011/0304862 A1 Dec. 15, 2011

(30) Foreign Application Priority Data

Jun. 15, 2010 (JP) .................................. 2010-136432

(51) Int. Cl.
*H04N 1/04* (2006.01)
(52) U.S. Cl.
USPC .............................. 358/475; 399/45; 356/448
(58) Field of Classification Search
USPC .............. 358/474, 1.9, 505, 509.475; 399/45; 356/445, 446, 448
See application file for complete search history.

(56) References Cited

U.S. PATENT DOCUMENTS

| 2003/0234373 A1 | 12/2003 | Chelvayohan et al. |
| 2004/0141764 A1 | 7/2004 | Runkowske et al. |
| 2008/0245979 A1 | 10/2008 | Banton et al. |
| 2009/0162089 A1* | 6/2009 | Ishibashi ......................... 399/74 |
| 2009/0231551 A1* | 9/2009 | Franik ............................ 353/69 |
| 2011/0304862 A1* | 12/2011 | Itoh et al. ....................... 358/1.9 |

FOREIGN PATENT DOCUMENTS

| DK | DE 10347334 A1 | 5/2004 |
| JP | 2004205463 A | 7/2004 |
| JP | 2005277678 A | 10/2005 |
| JP | 2006139179 A | 6/2006 |
| JP | 2006139180 A | 6/2006 |
| JP | 2008256691 A | 10/2008 |
| JP | 2009068891 A | 4/2009 |

OTHER PUBLICATIONS

European Search report dated May 28, 2013, in corresponding European Application No. 11169145.7-1504.
European Search report dated May 31, 2013 in corresponding European Application No. 11169145.7-1504.

* cited by examiner

*Primary Examiner* — Kimberly A Williams
(74) *Attorney, Agent, or Firm* — Harness, Dickey & Pierce, P.L.C.

(57) ABSTRACT

An image inspecting apparatus includes a first light illuminating unit irradiating a measured object on which an image is formed with light from an inclined direction; a second light illuminating unit irradiating the measured object with light from a different direction; an imaging unit receiving reflected light of the light with which the measured object is irradiated by the first light illuminating unit and the second light illuminating unit; a first and a second reference plate having a mirror surface and a diffuse surface, respectively; and an image inspecting unit inspecting a gloss distribution of the image based on the amount of light received by the imaging unit and a correcting coefficient.

13 Claims, 19 Drawing Sheets

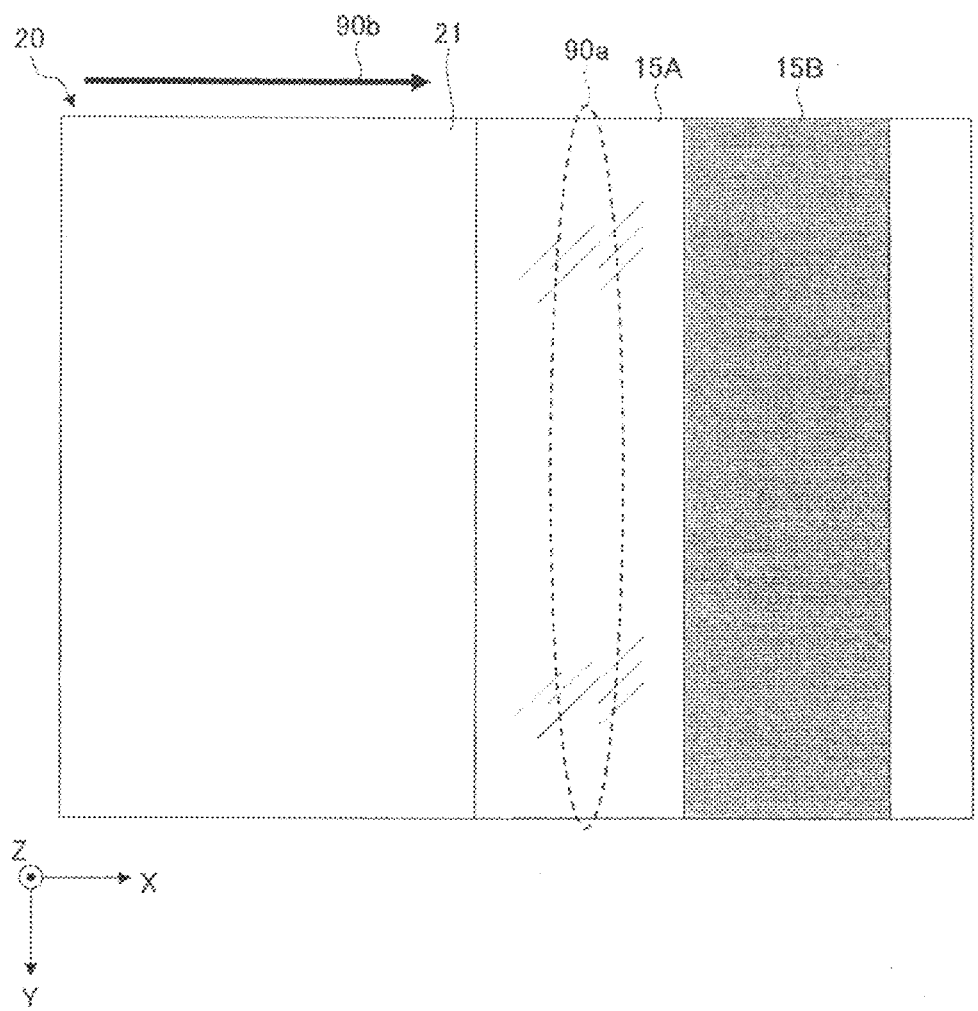

IMAGE INSPECTING APPARATUS, IMAGE INSPECTING METHOD, AND IMAGE FORMING APPARATUS

BACKGROUND OF THE INVENTION

1. Field of the Invention

The present invention relates to a method and an apparatus for inspecting a measured object on which an image is formed, and an image forming apparatus.

2. Description of the Related Art

Various printing machines have been proposed which are capable of imparting gloss to a printed item. For example, gloss may be imparted by using a UV varnish, a transparent ink that does not penetrate paper, or by forming dots using a transparent toner. Thus, various gloss distribution inspecting apparatuses have been proposed for inspecting gloss irregularity as well as a density distribution of the printed item.

For example, Japanese Laid-open Patent Publication No. 2005-277678 (Patent Document 1) discusses an apparatus for acquiring density distribution and gloss degree distribution data of a printed item. The apparatus acquires the data by measuring specular reflected light and diffuse reflected light from the printed item as image data by using a camera and two illuminating units.

In order to acquire the gloss degree distribution, data consisting solely of specular reflected light is required. However, when the apparatus discussed in Patent Document 1 is simply applied, it is difficult to image only the specular reflected light with the camera, and the obtained data may include the diffuse reflected light. In addition, in the case of white paper, the specular reflected light may be buried in the strong diffuse reflected light from the white paper.

Further, Patent Document 1 does not discuss any structure for separating the data based on light including both the specular reflected light and the diffuse reflected light into data based solely on the specular reflected light and data based solely on the diffuse reflected light.

SUMMARY OF THE INVENTION

In one aspect of the present invention, an image inspecting apparatus includes a first light illuminating unit configured to irradiate a measured object on which an image is formed with illuminating light from an inclined direction; a second light illuminating unit configured to irradiate the measured object with illuminating light from a direction different from the inclined direction of the first light illuminating unit; an imaging unit configured to receive reflected light of the illuminating light with which the measured object is irradiated by the first light illuminating unit, and reflected light of the illuminating light with which the measured object is irradiated by the second light illuminating unit; a first reference plate having a mirror surface and configured to be disposed instead of the measured object; a second reference plate having a diffuse surface and configured to be disposed instead of the measured object; and an image inspecting unit configured to inspect the image. The image inspecting unit calculates a correcting coefficient based on a ratio of an amount of reflected light of illuminating light that is received by the imaging unit when the diffuse surface of the second reference plate is irradiated with the illuminating light from the first light illuminating unit to an amount of reflected light of illuminating light that is received by the imaging unit when the diffuse surface of the second reference plate is irradiated with the illuminating light from the second light illuminating unit. The image inspecting unit inspects a gloss distribution of the image based on a value obtained by shading-correcting an amount of light obtained by subtracting an amount of reflected light of illuminating light that is received by the imaging unit when the measured object is irradiated with the illuminating light from the second light illuminating unit multiplied by the correcting coefficient, from an amount of reflected light of the illuminating light that is received by the imaging unit when the measured object is irradiated with the illuminating light from the first light illuminating unit, by using an amount of reflected light of illuminating light that is received by the imaging unit when the mirror surface of the first reference plate is irradiated with the illuminating light from the first light illuminating unit.

In another aspect, an image inspecting method includes a first step of irradiating a diffuse surface of a second reference plate with illuminating light from a first light illuminating unit in an inclined direction, and receiving reflected light of the illuminating light with an imaging unit; a second step of irradiating the diffuse surface of the second reference plate with illuminating light from a second light illuminating unit in a direction different from the inclined direction of the first step, and receiving reflected light of the illuminating light with the imaging unit; a third step of irradiating a mirror surface of a first reference plate with illuminating light from the first light illuminating unit in the inclined direction, and receiving reflected light of the illuminating light with the imaging unit; a fourth step of calculating a correcting coefficient based on a ratio of an amount of the reflected light received in the first step to an amount of the reflected light received in the second step; a fifth step of irradiating a measured object on which an image is formed with illuminating light from the first light illuminating unit in an inclined direction, and receiving reflected light of the illuminating light with the imaging unit; a sixth step of irradiating the measured object with illuminating light from the second light illuminating unit in a direction different from the inclined direction of the fifth step, and receiving reflected light of the illuminating light with the imaging unit; and a seventh step of inspecting a gloss distribution of the image based on a value obtained by shading-correcting an amount of light obtained by subtracting a value obtained by multiplying an amount of reflected light of the illuminating light with which the measured object is irradiated in the sixth step with the correcting coefficient, from an amount of reflected light of the illuminating light with which the measured object is irradiated in the fifth step, by using an amount of the reflected light received in the third step.

In another aspect of the present invention, an image forming apparatus for forming an image on an image carrying medium includes the image inspecting apparatus. The image inspecting apparatus is configured to inspect one or both of a gloss distribution and a density distribution of the image formed on the image carrying medium.

BRIEF DESCRIPTION OF THE DRAWINGS

FIG. 5A is a plan view of a reference plate moving apparatus;

DETAILED DESCRIPTION OF THE PREFERRED EMBODIMENTS

Figure 1:
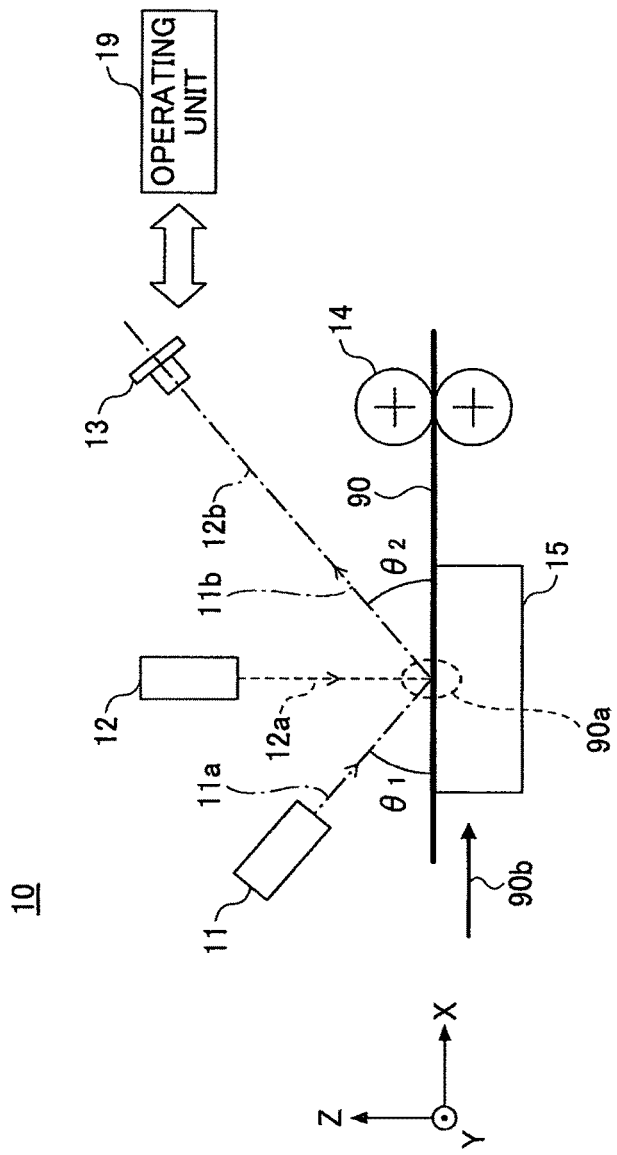
FIG. 1 is a side view of an image inspecting apparatus according to a first embodiment of the present invention.

Embodiments of the present invention are described in the following with reference to the attached drawings, wherein like reference numerals may designate identical or corresponding parts throughout the several views.

First Embodiment

Figure 2:
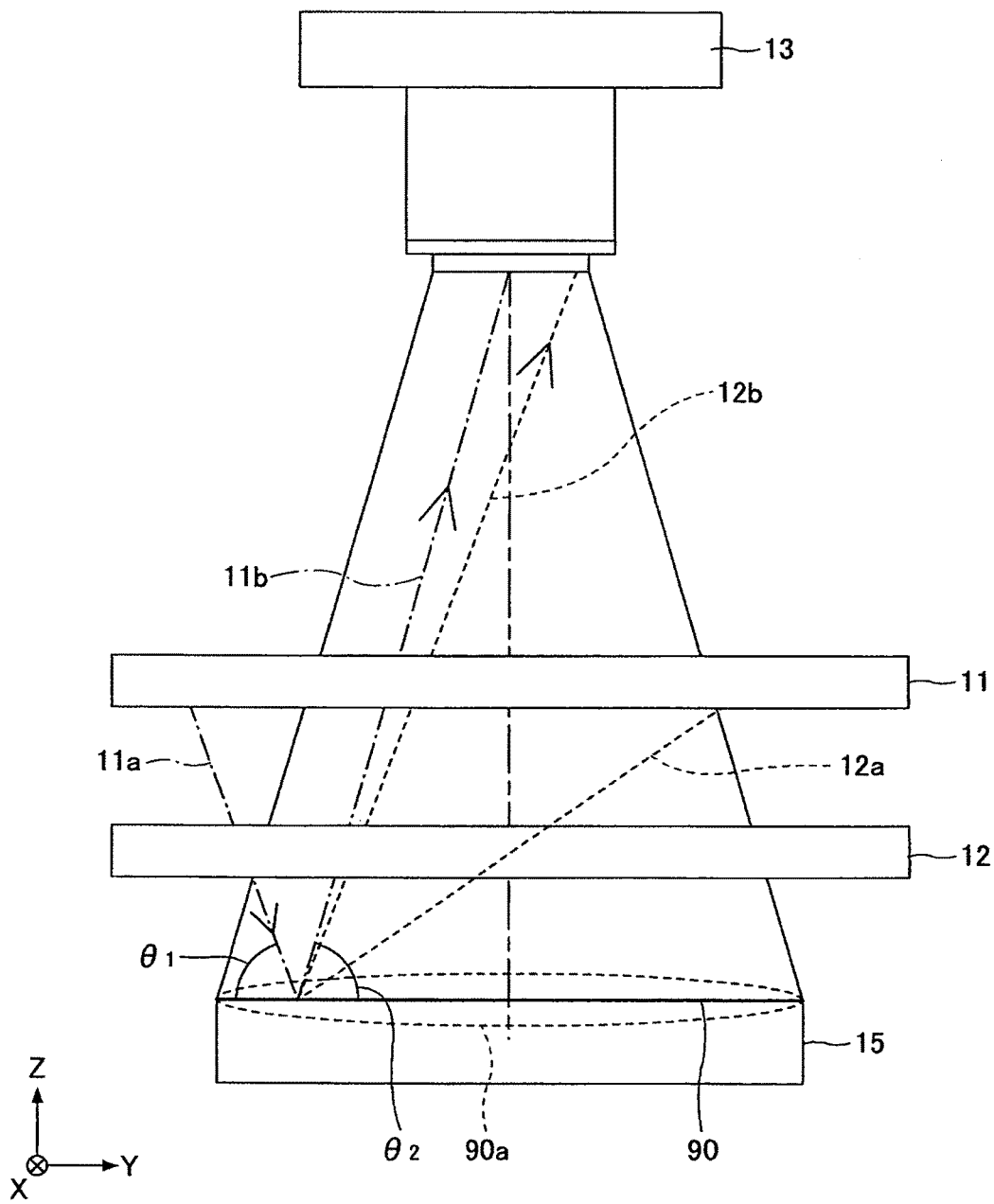
FIG. 2 is front view of the image inspecting apparatus according to the first embodiment.

FIG. 1 is a side view of an image inspecting apparatus 10 according to a first embodiment of the invention. FIG. 2 is a front view of the image inspecting apparatus 10. Some of the elements or components illustrated in FIG. 1 are not illustrated in FIG. 2 for sake of ease of description.

With reference to FIGS. 1 and 2, the image inspecting apparatus 10 includes a gloss illuminating apparatus 11, a density illuminating apparatus 12, an imaging element 13, a transport unit 14, and a reference plate 15. An image carrying medium 90 as a measured object may include a sheet of paper. Numeral 90a designates a line of a reading area (which may be hereafter referred to as "the reading area 90a") of which a gloss distribution and a density distribution may be read by the image inspecting apparatus 10. Numeral 90b designates a direction of transport of the image carrying medium 90 (which may be hereafter referred to as the "transport direction"). An imaging lens may be disposed in front of the imaging element 13. In the example illustrated in FIGS. 1 and 2, the transport direction corresponds to an X direction (sub-scan direction); a direction perpendicular to the X direction in a plane on which the image carrying medium 90 is disposed is referred to as a Y direction (main scan direction); and a direction perpendicular to the X direction and the Y direction is referred to as a Z direction.

In the following description, the "specular reflected light" refers to reflected light that is reflected in a direction opposite to a direction in which illuminating light 11a from the gloss illuminating apparatus 11 that irradiates the image carrying medium 90, with the same angle as the angle of incidence of the illuminating light 11a. The "diffuse reflected light" refers to reflected light other than the specular reflected light.

The gloss illuminating apparatus 11 has the function of irradiating the reading area 90a (one line along the Y direction of the image carrying medium 90) of the image carrying medium 90 with the illuminating light 11a at a predetermined incident angle $\theta_1$. Numeral 11b designates the specular reflected light produced by the reflection of the illuminating light 11a, which is incident on the reading area 90a of the image carrying medium 90 at the incident angle $\theta_1$, from the reading area 90a. Thus, the incident angle $\theta_1$ is equal to the reflection angle $\theta_2$. According to the JIS (Japanese Industrial Standards), incident angle and reflection angle for measuring a gloss degree are specified to be 20°, 45°, 60°, 75°, and 85°, of which 60° is generally widely employed.

The gloss illuminating apparatus 11 may include plural light-emitting elements arranged along a direction parallel to the reading area 90a (Y direction) of the image carrying medium 90. The light-emitting elements may include light emitting diodes (LEDs) or organic electro-luminescence (EL) elements. Particularly, the LED is suitable as a light-emitting element according to the present embodiment because of its high directionality of light emission compared to other light sources, such as a fluorescent lamp, which reduces the amount of outgoing light in other directions and therefore reduces the likelihood of development of flair light. The gloss illuminating apparatus 11 is an example of a first light illuminating unit. The number of light-emitting elements in the gloss illuminating apparatus 11 may be determined as needed. Preferably, the light-emitting elements may be disposed in a closely arranged manner in order to produce the illuminating light that causes the specular reflected light from the entire reading area 90a of the image carrying medium 90.

The density illuminating apparatus 12 has the function of irradiating the reading area 90a of the image carrying medium 90 with illuminating light 12a at a predetermined angle. The "predetermined angle" may be an angle different from the incident angle $\theta_1$. For example, the predetermined angle may be 90°. The density illuminating apparatus 12 may include a diffuse illuminating apparatus, such as a xenon lamp or an LED array. The gloss illuminating apparatus 11 and the density illuminating apparatus 12 do not emit light at the same time. Preferably, the gloss illuminating apparatus 11 and the density illuminating apparatus 12 may be configured to emit light alternately in accordance with the operation of the imaging element 13, or either one may be configured to emit light as needed. The density illuminating apparatus 12 is an example of a second light illuminating unit.

The imaging element 13 may include plural pixels arranged along a direction (Y direction) parallel to the reading area 90a of the image carrying medium 90. The imaging element 13 has the function of acquiring the amount of the specular reflected light 11b of the illuminating light 11a with which the reading area 90a of the image carrying medium 90 is irradiated by the gloss illuminating apparatus 11. The imaging element 13 also has the function of acquiring the amount of the diffuse reflected light 12b of the illuminating light 12a with which the reading area 90a of the image carrying medium 90 is irradiated by the density illuminating apparatus 12. Thus, the imaging element 13 is disposed at a position enabling the imaging element 13 to image the specular reflected light and the diffuse reflected light of the illuminating light with which the reading area 90a of the image carrying medium 90 is irradiated by the gloss illuminating apparatus 11.

The imaging element 13 may include a MOS (Metal Oxide Semiconductor) device, a CMOS (Complimentary Metal Oxide Semiconductor) device, a CCD (Charge Coupled Device), or a CIS (Contact Image Sensor). When a color image is imaged; an imaging element of a three-line type that is sensitive to each of the RGB colors may be used. The imaging element 13 is an example of an imaging unit.

The transport unit 14 transports the image carrying medium 90 in the transport direction 90b (X direction in FIG. 1). The reference plate 15 may include a substantially rectangular-solid plate configured to be disposed at the reading area 90a in a replaceable manner. The reference plate 15 is normally not moved from the reading area 90a, and only the image carrying medium 90 is transported over the reference plate 15 in the transport direction 90b by the transport unit 14. Preferably, plural reference plates may be configured to be disposed in sequence at the reading area 90a by using a reference plate moving apparatus 20, as will be described later.

The operating unit 19 has the function of executing various operating processes by acquiring the data of the amount of specular reflected light or diffuse reflected light received by the imaging element 13 as image data. The operating unit 19 may include a CPU (central processing unit) and a memory, such as a ROM or a RAM, which are not illustrated. The memory (not illustrated) of the operating unit 19 may store a program for inspecting gloss distribution. Various functions of the operating unit 19 may be realized when the program is executed by the CPU (not illustrated). Alternatively, the program for inspecting gloss distribution may be stored in a computer-readable recording medium, such as an optical recording medium or a magnetic recording medium. The operating unit 19 is an example of an image inspecting unit.

The image inspecting apparatus 10 performs a gloss distribution and density distribution inspecting process as follows. First, the image inspecting apparatus 10 turns on the gloss illuminating apparatus (while turning off the density illuminating apparatus 12) and irradiates one line of the reading area 90a with the illuminating light 11a. Then, the imaging element 13 acquires the amount of the specular reflected light 11b from the reading area 90a. Based on the amount of the specular reflected light 11b, the gloss distribution of the reading area 90a is inspected. Then, the image inspecting apparatus 10 turns on the density illuminating apparatus 12 (while turning off the gloss illuminating apparatus 11) and irradiates the one line of the reading area 90a with the illuminating light 12a. The amount of the diffuse reflected light 12b from the reading area 90a is acquired by the imaging element 13. Based on the amount of the diffuse reflected light 12b, the density distribution of the reading area 90a is inspected, thus completing the inspection of the gloss distribution and the density distribution of the one line (one dimension).

After the inspection of the gloss distribution and the density distribution of the one line is completed, the transport unit 14 transports the image carrying medium 90 in the transport direction 90b by a predetermined distance. Thereafter, the next line (one dimension) is inspected in the same way as described above. By repeating this process, a two-dimensional gloss distribution and density distribution inspection can be performed.

However, in the above-described structure of the image inspecting apparatus 10 alone, the specular reflected light cannot be exclusively measured by the imaging element 13; namely, some of the diffuse reflected light may also be measured. Thus, in accordance with the present embodiment, the light amount data acquired by the imaging element 13 is corrected by using the reference plate 15.

The reference plate 15 may include two reference plates for different purposes, such as a reference plate 15A having a mirror surface and a reference plate 15B having a diffuse surface. Preferably, the mirror surface of the reference plate 15A is a perfect mirror surface having no diffuse reflection at all. Preferably, the diffuse surface of the reference plate 15B is a perfect diffuse surface from which light is reflected with equal luminance in every direction.

Figure 3A:
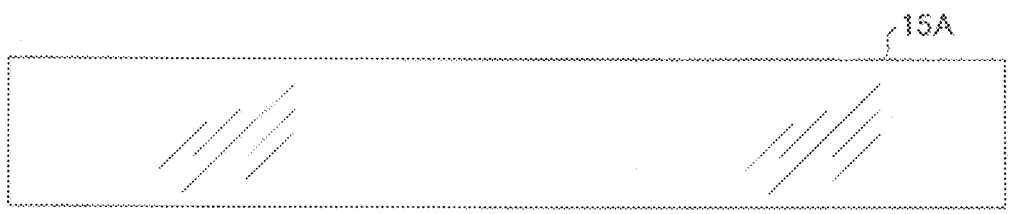
FIG. 3A illustrates an example of the characteristics of a reference plate 15A.
Figure 3B:
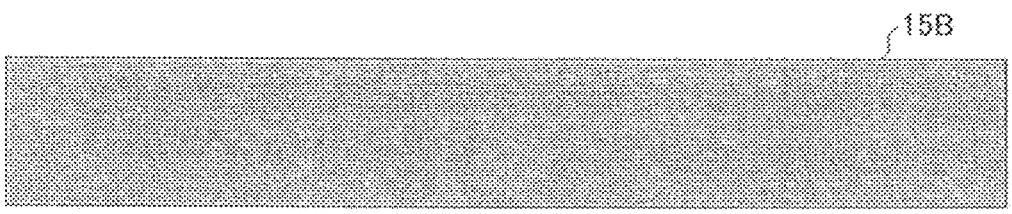
FIG. 3B illustrates an example of the characteristics of a reference plate 15B.

FIG. 3A illustrates an example of the characteristics of the reference plate 15A. As illustrated in FIG. 3A, the reference plate 15A may include a mirror surface with a gloss degree of 100%. FIG. 3B illustrates an example of the characteristics of the reference plate 15B. As illustrated in FIG. 3B, the reference plate 15B may include a white diffuse surface with a gloss degree of 0%. The reference plate 15A is an example of a first reference plate, and the reference plate 15B is an example of a second reference plate.

Figure 4A:
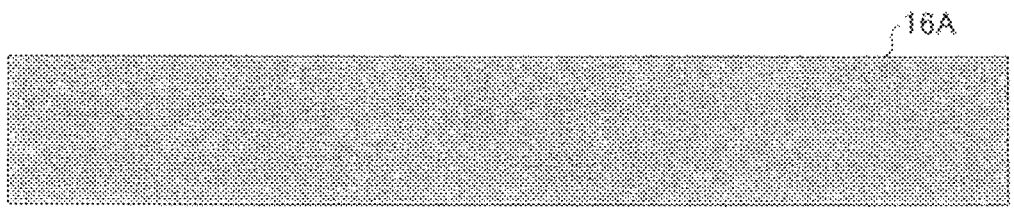
FIG. 4A illustrates an example of the characteristics of a reading background 16A.
Figure 4B:
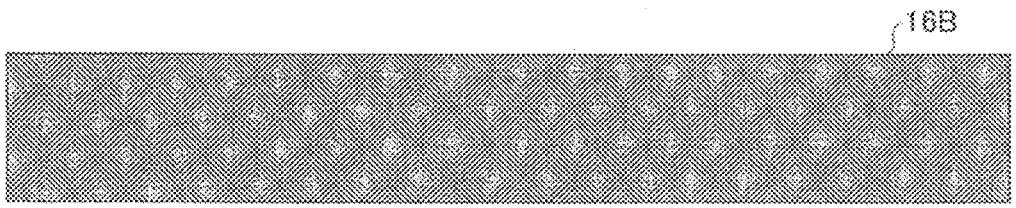
FIG. 4B illustrates an example of the characteristics of a reading background 16B.
Figure 4C:
FIG. 4C illustrates an example of the characteristics of a reading background 16C.

When the measured object (image carrying medium 90) is imaged, the measured object is placed on the reference plate 15A or 15B. Preferably, an appropriate reading background is disposed between the measured object and the reference plate 15A or 15B. FIGS. 4A, 4B, and 4C illustrate examples of the reading background. FIG. 4A illustrates an example of the characteristics of a reading background 16A. The reading background 16A is white with a gloss degree of 0%. FIG. 4B illustrates an example of the characteristics of a reading background 16B. The reading background 16B is black with a gloss degree of 0%. FIG. 4C illustrates an example of the characteristics of a reading background 16C. The reading background 16C may include glass or a half mirror.

When the white reading background 16A (FIG. 4A) is used, if the measured object is thin, such as a thin sheet of paper, the light may penetrate the measured object, so that the reflected light from the reading background 16A may also be imaged. In such a case, the amount of the reflected light of the light that has penetrated through the measured object to the reading background 16B can be reduced by using the black reading background 16B (FIG. 4B) as the reading background, thus increasing the accuracy of gloss distribution inspection. Preferably, the imaged amount of light may be reduced by using the reading background 16C (FIG. 4C) in order to reduce the reflected light from the reading background by diverting the light by the glass or half mirror.

When the measured object of the density distribution inspection is a white sheet of paper, the white reading background 16A (FIG. 4A) may be used so that the paper and a printed character or figure can be clearly distinguished. Namely, the reading background may be preferably changed depending on the type of the measured object or measurement data (such as whether gloss data or density data, for example).

Figure 5B:
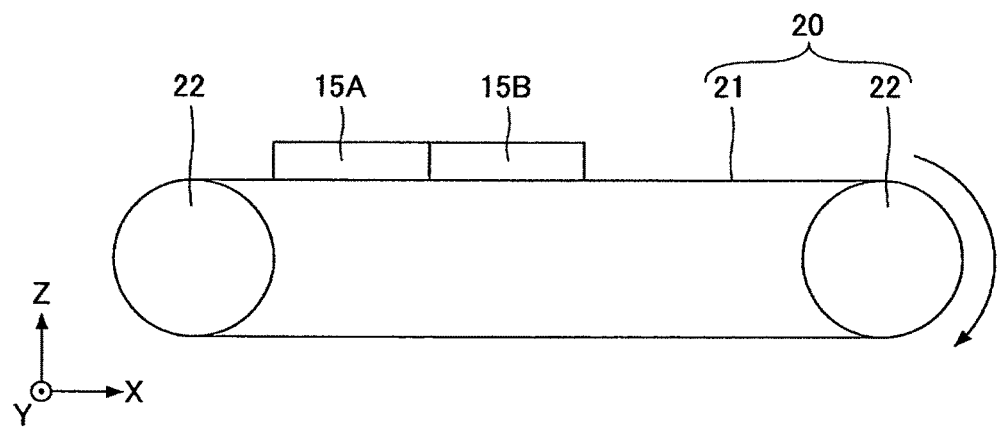
FIG. 5B is a side view of the reference plate moving apparatus.

The reference plates 15A and 15B may be disposed automatically at the reading area 90a by using a reference plate moving apparatus 20. FIG. 5A is a plan view of the reference plate moving apparatus 20. FIG. 5B is a side view of the reference plate moving apparatus 20. As illustrated in FIGS. 5A and 5B, the reference plate moving apparatus 20 includes a belt 21 and a belt drive unit 22. The belt 21 is driven by the belt drive unit 22 and transported in the transport direction 90b. On the belt 21, the reference plates 15A and 15B may be fixedly attached adjacent to each other.

When the belt drive unit 22 is driven, the reference plates 15A and 15B are moved in the transport direction 90b together with the belt 21. As a result, the reference plate that is disposed at the reading area 90a can be automatically changed (the reference plate 15A or 15B). Further, by placing any of the reading backgrounds 16A, 16B, and 16C on the reference plates 15A and 15B, the reference plate 15A or 15B on which the reading background is placed can be automatically disposed at the reading area 90a by using the reference plate moving apparatus 20.

Next, a calibrating process in the image inspecting apparatus 10 involving the reference plates 15A and 15B is described. The image inspecting apparatus 10 may be calibrated at the time of initial setting, or in response to disturbance that affects the image inspecting apparatus 10, such as a change in the illuminating light or environment. During the calibrating process, only the reference plate is disposed at the reading area 90a without disposing the measured object, i.e., the image carrying medium 90, or the reading background at the reading area 90a.

Figure 6:
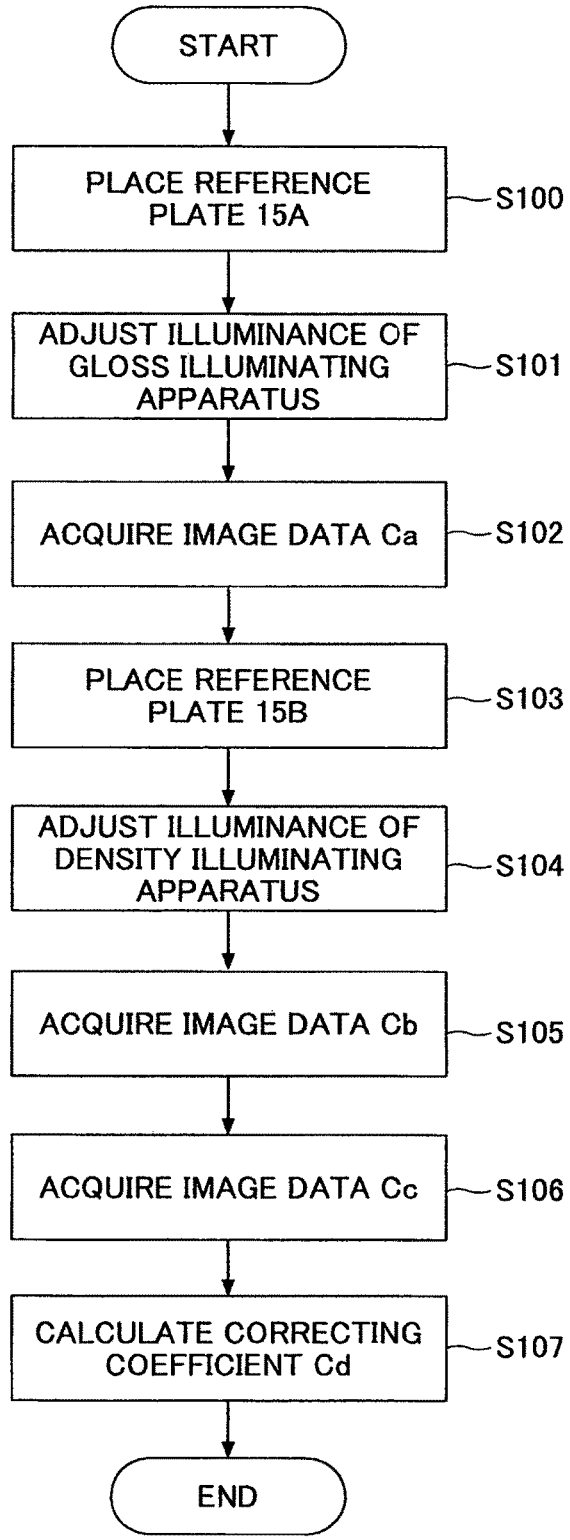
FIG. 6 is a flowchart of an example of an image inspecting apparatus calibrating process.
Figure 7:
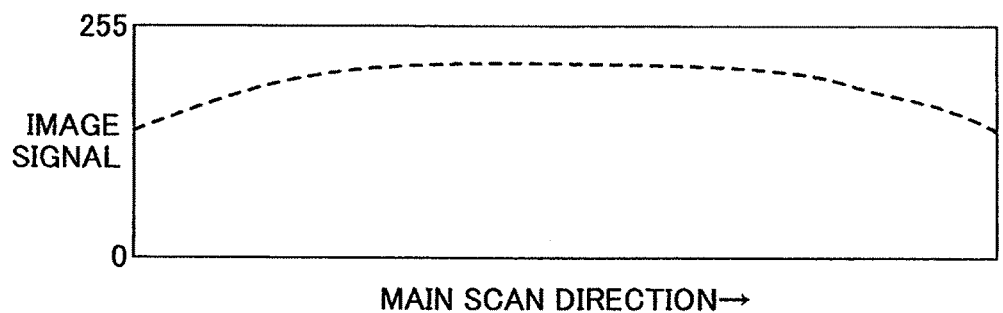
FIG. 7 illustrates an example of image data Ca acquired by an imaging element 13.

FIG. 6 is a flowchart of an example of the calibrating process for the image inspecting apparatus. In step S100, the reference plate 15A is disposed at the reading area 90a of the image inspecting apparatus 10. In step S101, illuminance of the gloss illuminating apparatus 11 is adjusted within the dynamic range of the imaging element 13. In step S102, only the gloss illuminating apparatus 11 is turned on, and the reflected light reflected by the reference plate 15A is acquired by the imaging element 13 as image data Ca. FIG. 7 illustrates an example of the image data Ca acquired by the imaging element 13. In FIG. 7, the horizontal axis corresponds to the main scan direction (Y direction in FIG. 1 or 5A, for example). The vertical axis corresponds to an image signal (i.e., the amount of the reflected light acquired by the imaging element 13).

Figure 8:
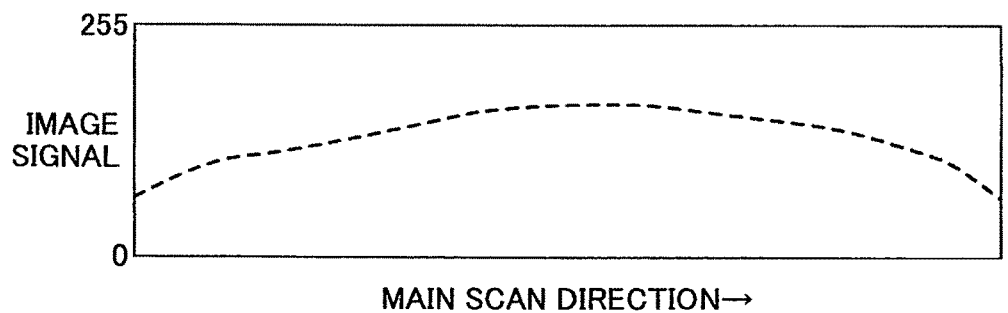
FIG. 8 illustrates an example of image data Cb acquired by the imaging element 13.

In step S103, the reference plate 15B is placed at the reading area 90a of the image inspecting apparatus 10, instead of the reference plate 15A. In step S104, illuminance of the density illuminating apparatus 12 is adjusted within the dynamic range of the imaging element 13. In step S105, only the gloss illuminating apparatus 11 is turned on, and the reflected light reflected by the reference plate 15B is acquired by the imaging element 13 as image data Cb. FIG. 8 illustrates an example of the image data Cb acquired by the imaging element 13. In FIG. 8, the horizontal axis and the vertical axis are as in FIG. 7.

Figure 9:
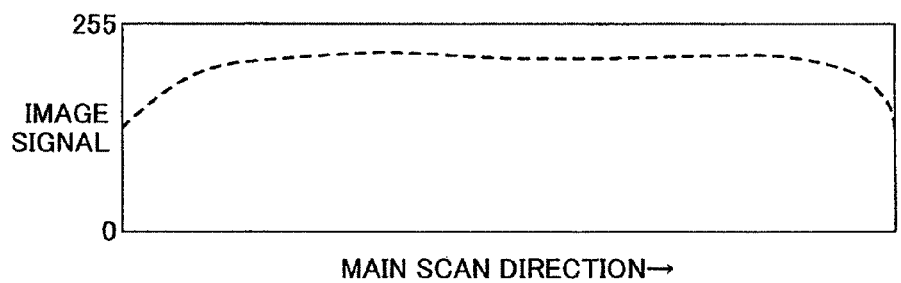
FIG. 9 illustrates an example of image data Cc acquired by the imaging element 13.

In step S106, only the density illuminating apparatus 12 is turned on, and the reflected light reflected by the reference plate 15B is acquired by the imaging element 13 as image data Cc. FIG. 9 illustrates an example of the image data Cc acquired by the imaging element 13. In FIG. 9, the horizontal axis and the vertical axis are as in FIG. 7.

In step S107, a correcting coefficient Cd is calculated. The correcting coefficient Cd may be calculated according to the following equation:

$$Cd = \text{Image data } Cb / \text{Image data } Cc \quad (1)$$

Figure 10:
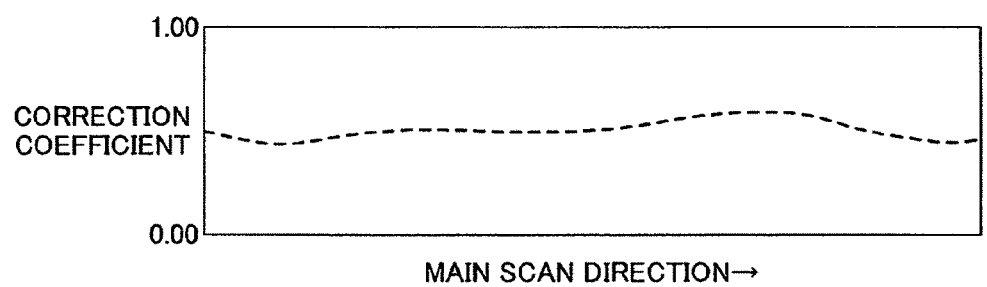
FIG. 10 illustrates an example of a correcting coefficient Cd calculated in step S107.

FIG. 10 illustrates an example of the correcting coefficient Cd calculated in step S107. In FIG. 10, the horizontal axis corresponds to the main scan direction (Y direction in FIG. 1 or 5A, for example), and the vertical axis corresponds to the correcting coefficient. Because the diffuse reflected light is reflected equally in every direction, the image data Cb and the image data Cc are of the diffuse reflected light with different scales and similar distributions, although there may be some errors between them. Thus, in order to eliminate the diffuse reflected light that enters the image data Cb, the difference in scale between the gloss illuminating apparatus 11 and the density illuminating apparatus 12 is corrected in accordance with the correcting coefficient Cd. By using the correcting coefficient Cd, only the diffuse reflected light that enters the image data Cb acquired by turning on only the gloss illuminating apparatus 11 can be estimated from the image data Cc acquired by turning on only the density illuminating apparatus 12.

Figure 11:
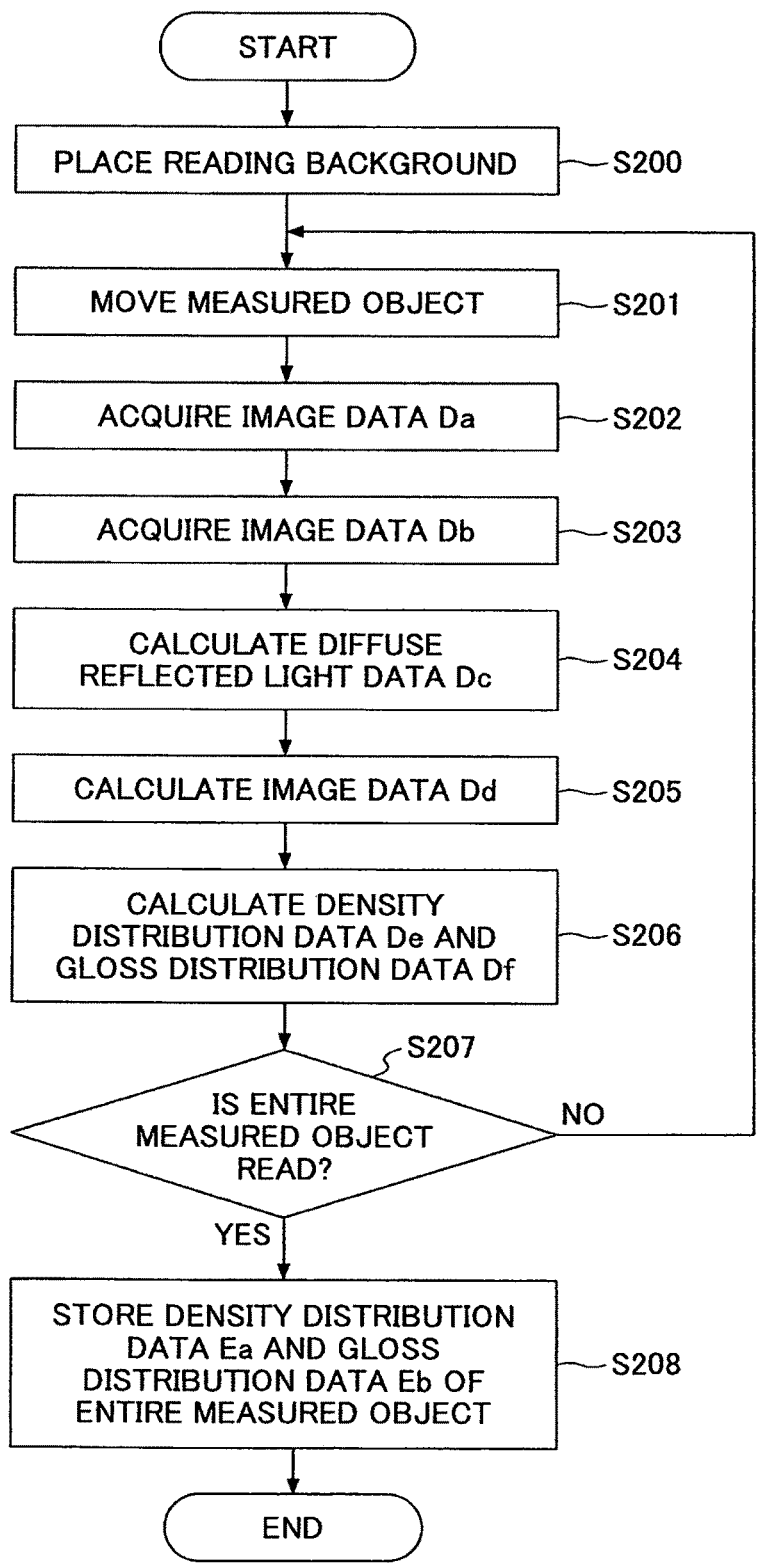
FIG. 11 is a flowchart of an image inspecting apparatus correcting process.

Next, a correcting process based on the correcting coefficient Cd in the image inspecting apparatus 10 is described. FIG. 11 is a flowchart of the correcting process in which image data of the measured object is acquired by using the correcting coefficient Cd. Referring to FIG. 11, in step S200, any one of the reading backgrounds 16A, 16B, and 16C (FIG. 4A, 4B, or 4C) is placed on the reference plate 15A. Then, in step S201, the measured object, i.e., the image carrying medium 90, is transported in the transport direction 90b by the transport unit 14 to the reading area 90a.

Figure 12:
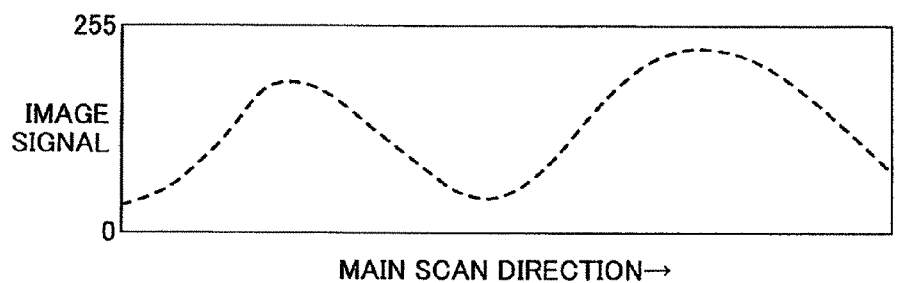
FIG. 12 illustrates an example of image data Da acquired by the imaging element.
Figure 13:
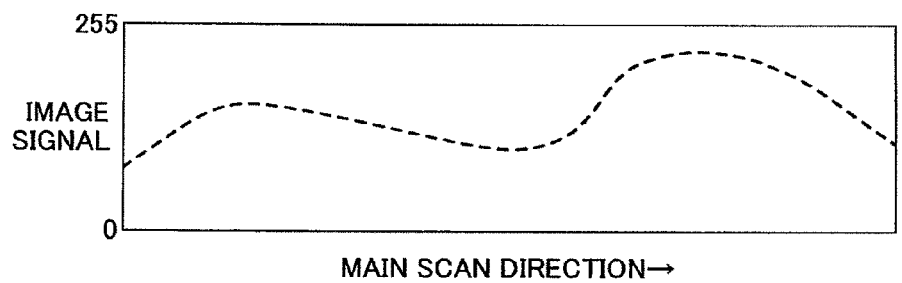
FIG. 13 illustrates an example of image data Db acquired by the imaging element 13.

In step S202, only the density illuminating apparatus 12 is turned on, and the reflected light reflected by the image carrying medium 90 is acquired by the imaging element 13 as image data Da. FIG. 12 illustrates an example of the image data Da acquired by the imaging element 13. In the example of FIG. 12, the horizontal axis and the vertical axis are as in FIG. 7. Then, in step S203, only the gloss illuminating apparatus 11 is turned on, and the reflected light reflected by the image carrying medium 90 is acquired by the imaging element 13 as image data Db. The reflected light mainly includes specular reflected light and also some diffuse reflected light. FIG. 13 illustrates an example of the image data Db acquired by the imaging element 13. In the example of FIG. 13, the horizontal axis and the vertical axis are as in FIG. 7.

In step S204, diffuse reflected light data Dc is calculated from the image data Da acquired in step S202, by using the correcting coefficient Cd calculated in step S107 of FIG. 7. The diffuse reflected light data Dc corresponds to the diffuse reflected light included in the reflected light in step S203. The diffuse reflected light data Dc may be calculated according to the following equation:

$$Dc = \text{Image data } Da \times \text{Correcting coefficient } Cd \quad (2)$$

Figure 14:
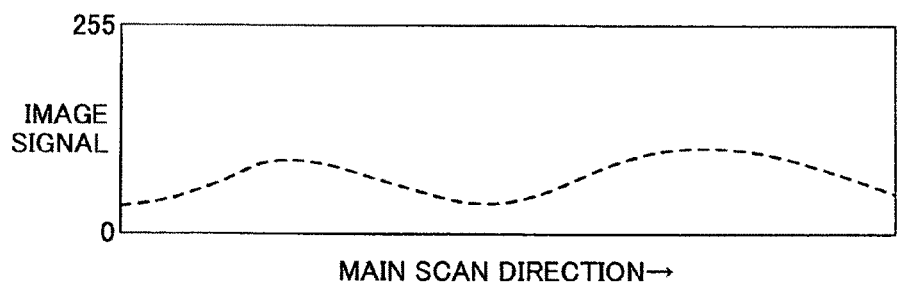
FIG. 14 illustrates an example of diffuse reflected light data Dc calculated in step S204.

FIG. 14 illustrates an example of the diffuse reflected light data Dc calculated in step S204. In FIG. 14, the horizontal axis and the vertical axis are as in FIG. 7.

In step S205, specular reflected light data Dd is calculated from the diffuse reflected light data Dc calculated in step S204. The specular reflected light data Dd corresponds to the specular reflected light included in the reflected light in step S203. The specular reflected light data Dd may be calculated according to the following equation:

$$Dd = \text{Image data } Db - \text{Diffuse reflected light data } Dc \quad (3)$$

Figure 15:
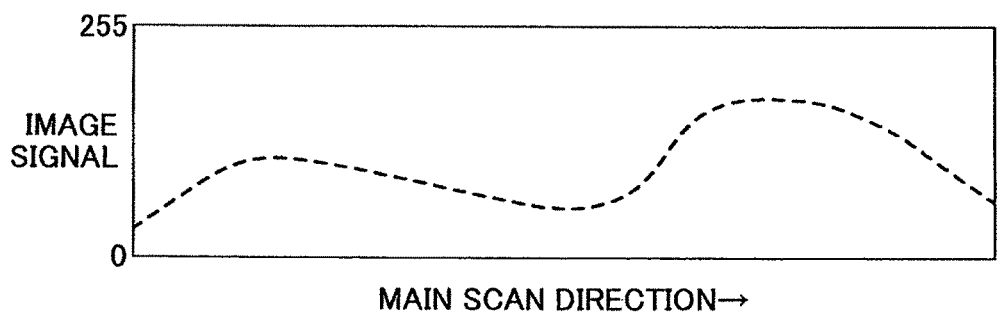
FIG. 15 illustrates an example of specular reflected light data Dd calculated in step S205.

FIG. 15 illustrates an example of the specular reflected light data Dd calculated in step S205. In FIG. 15, the horizontal axis and the vertical axis are as in FIG. 7.

In step S206, shading correction is performed, and density distribution data De and gloss degree distribution data Df are calculated. The density distribution data De may be calculated according to the following equation:

$$De = 255 \times \text{Image data } Da/\text{Image data } Cc \quad (4)$$

The gloss degree distribution data Df may be calculated according to the following equation:

$$Df = 255 \times \text{Image data } Dd/\text{Image data } Ca \quad (5)$$

Figure 16:
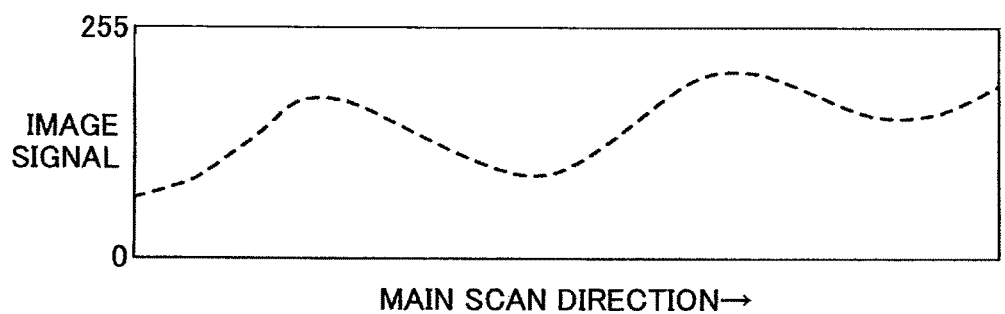
FIG. 16 illustrates an example of density distribution data De calculated in step S206.
Figure 17:
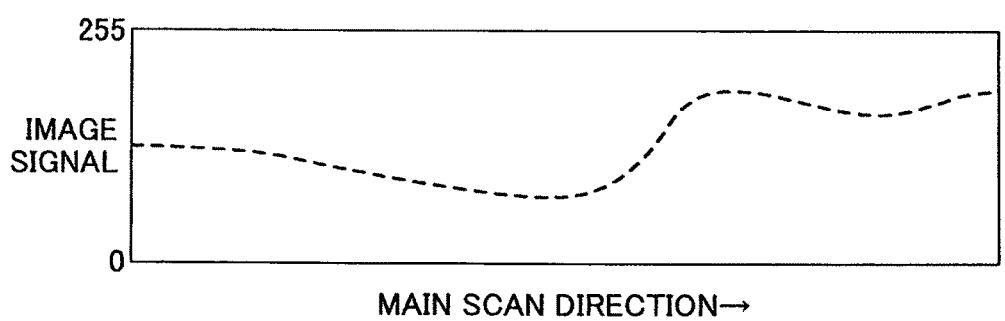
FIG. 17 illustrates an example of gloss degree distribution data Df calculated in step S206.

FIG. 16 illustrates an example of the density distribution data De calculated in step S206. FIG. 17 illustrates an example of the gloss degree distribution data Df calculated in step S206. In FIGS. 16 and 17, the horizontal axis and the vertical axis are as in FIG. 7. Thus, the process of reading one line is completed. The shading correction may involve the correction of distortion in a signal due to variations in the sensitivity of the imaging element 13 or limb darkening of an optical system.

In step S207, it is determined whether the measured object, i.e., the image carrying medium 90, has been entirely read. When it is determined that the image carrying medium 90 is not entirely read ("No"), the process returns to step S201 and the above process is repeated. Namely, the image carrying medium 90 is transported by the transport unit 14 in the X direction of FIG. 1 by a predetermined distance, and the density distribution data De and the gloss distribution data Df are calculated for the next one line (one dimension). By repeating this operation, density distribution data Ea and gloss distribution data Eb of the entire image carrying medium 90 (two dimension) can be calculated, which is a collection of the density distribution data De and the gloss distribution data Df of the lines (one dimension).

When it is determined in step S207 that the entire image carrying medium 90 has been read ("Yes"), the density distribution data Ea and the gloss distribution data Eb of the entire image carrying medium 90 (two dimension) may be stored in an external storage apparatus in step S208. Preferably, the density distribution data Ea and the gloss distribution data Eb may be outputted to an external output apparatus as needed.

Thus, in accordance with the first embodiment, the two reference plates 15A and 15B with different purposes are provided in the image inspecting apparatus 10, and the image data is corrected in consideration of deviation in the illuminance distribution of the gloss illuminating apparatus 11 or the density illuminating apparatus 12, or the difference in intensity of the specular reflected light and the diffuse reflected light acquired by the imaging element 13. Thus, the data based on light that includes the specular reflected light and the diffuse reflected light can be accurately separated into the data based solely on the specular reflected light and the data based solely on the diffuse reflected light. In this way, the gloss degree distribution and the density distribution can be inspected in a highly reliable manner.

Second Embodiment

Figure 18:
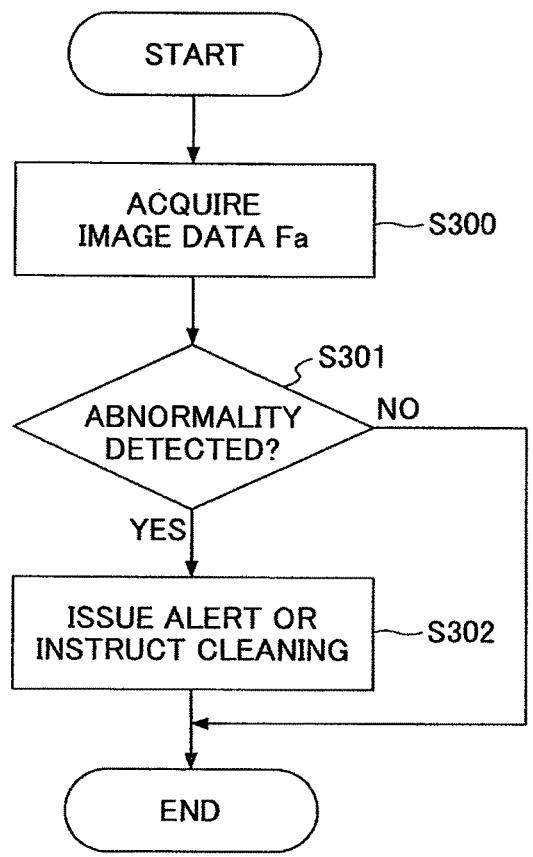
FIG. 18 is a flowchart of an abnormality process performed in the image inspecting apparatus.

In accordance with the second embodiment, prior to the calibrating process (see FIG. 6) of the image inspecting apparatus, an abnormality process is performed upon detection of abnormality, such as the presence of dirt on the reference plate. FIG. 18 is a flowchart of an example of the abnormality process in the image inspecting apparatus, which is performed prior to step S102 of FIG. 6.

Figure 19:
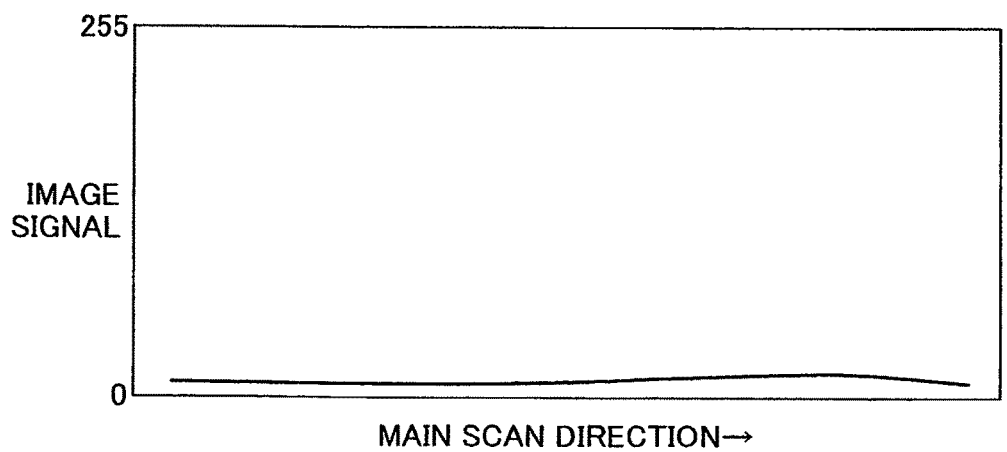
FIG. 19 illustrates a first example of image data Fa acquired by the imaging element 13.
Figure 20:
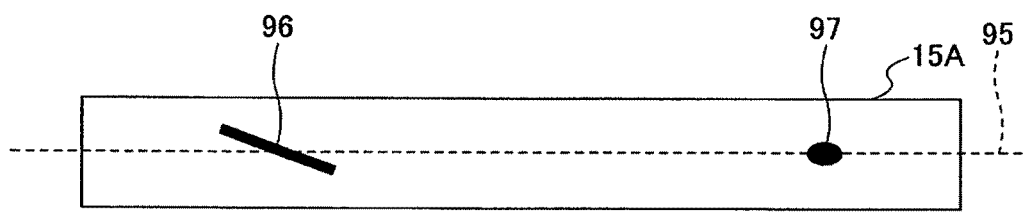
FIG. 20 illustrates the presence of foreign matter on a reading position of a reference plate.
Figure 21:
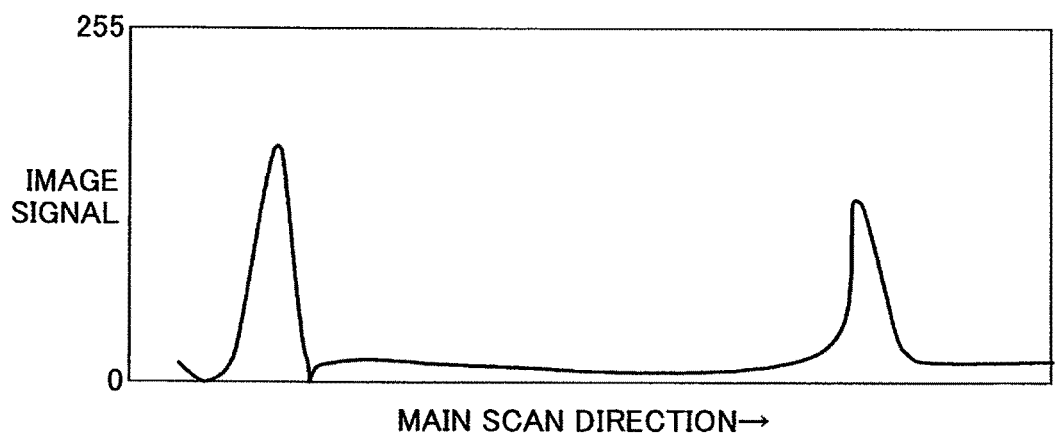
FIG. 21 illustrates a second example of the image data Fa acquired by the imaging element 13.

In step S300, only the density illuminating apparatus 12 is turned on, and the reflected light reflected by the reference plate 15A is acquired by the imaging element 13 as image data Fa. The density illuminating apparatus 12 is disposed at an angle such that no specular reflected light becomes incident on the imaging element 13. Therefore, when the reference plate 15A is normal (i.e., without dust or dirt), the image data Fa is substantially zero, as illustrated in FIG. 19. However, when there is foreign matter 96 or 97, such as dust or dirt, on a reading position 95 of the reference plate 15A as illustrated in FIG. 20, the light is diffuse-reflected only by the portions where the foreign matter 96 or 97 is present. As a result, the image data Fa exhibits high values corresponding to the portions of the foreign matter 96 or 97, as illustrated in FIG. 21. In FIGS. 19 and 21, the horizontal axis and the vertical axis are as in FIG. 7.

In step S301, abnormality in the image data Fa is detected. Specifically, it is determined whether the image data Fa acquired in step S300 is equal to or more than a predetermined threshold value Th. When it is determined in step S301 that the threshold value Th is reached or exceeded ("Yes"), the user may be alerted to the presence of the foreign matter 96 or 97 on the reference plate 15A or instructed to clean the reference plate 15A in step S302. When it is determined in step S301 that the image data Fa is less than the threshold value Th ("No"), it is determined that there is no foreign matter 96 or 97 on the reference plate 15A, and the abnormality process is completed.

Thus, in accordance with the second embodiment, in addition to the effects of the first embodiment, the following effect can be obtained. Namely, by detecting the presence of foreign matter, such as dust or dirt, on the reference plate, the user can be alerted to the presence of the dust or dirt or instructed to clean the reference plate, thus preventing the measurement of abnormal gloss degree distribution data.

Third Embodiment

In accordance with the third embodiment, it is determined whether the incident angle and the reflection angle are equally set. When they are not equally set, the angle of the gloss illuminating apparatus or the imaging element is adjusted such that the incident angle and the reflection angle are equal to each other.

As mentioned above, according to the JIS, incident angle and reflection angle for measuring a gloss degree are specified to be 20°, 45°, 60°, 75°, and 85°, of which 60° is generally widely utilized. However, even when the incident angle and the reflection angle are accurately adjusted at the time of factory shipment, the position of the gloss illuminating apparatus 11 or the imaging element 13 may be displaced during later transport, for example, resulting in disagreement between the incident angle and the reflection angle.

Figure 22:
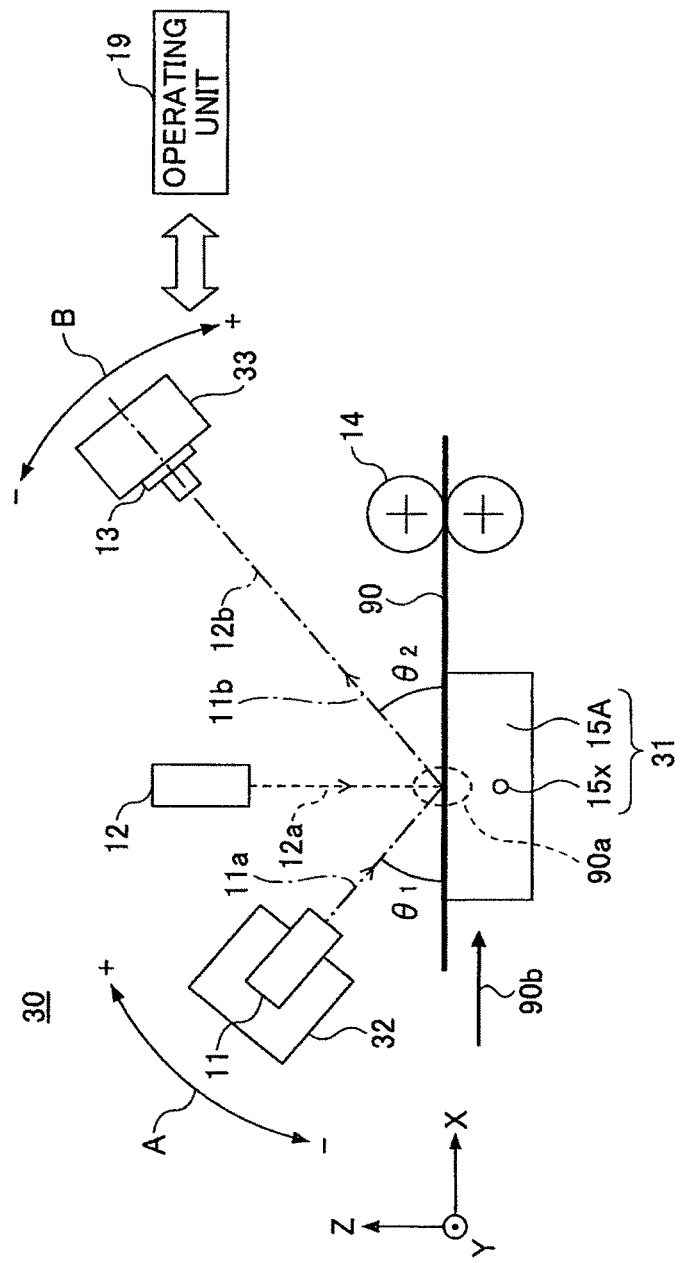
FIG. 22 illustrates an image inspecting apparatus according to a third embodiment.

FIG. 22 illustrates an example of an image inspecting apparatus 30 according to the third embodiment. The image inspecting apparatus 30 differs from the image inspecting apparatus 10 (see FIGS. 1 and 2) in that the image inspecting apparatus 30 includes a reference plate angle changing apparatus 31, a gloss illumination angle changing apparatus 32, and an imaging element angle changing apparatus 33. In the following, the image inspecting apparatus 30 is described by mainly focusing on the difference from the image inspecting apparatus 10.

Figure 23:
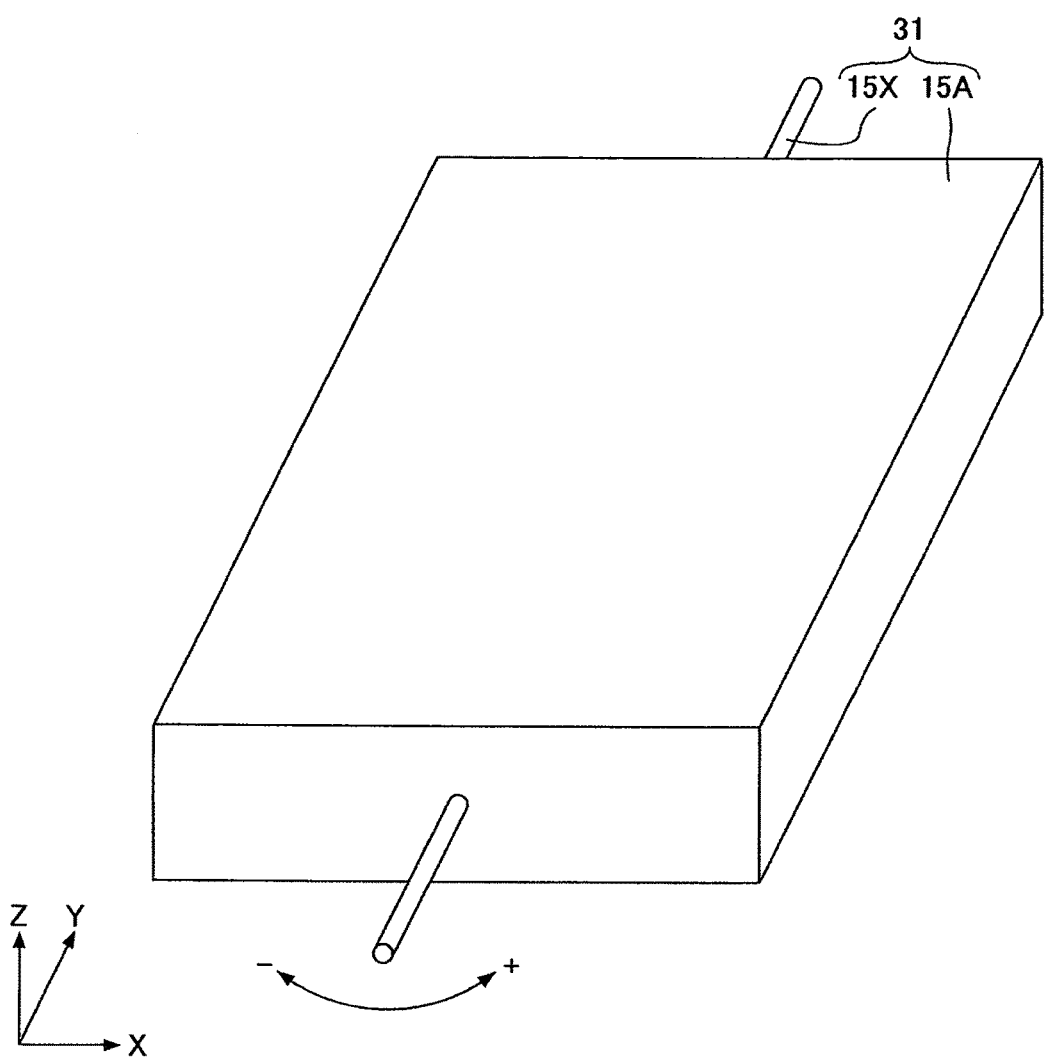
FIG. 23 is a perspective view of a reference plate angle changing apparatus.

FIG. 23 is a perspective view of an example of the reference plate angle changing apparatus 31. As illustrated, the reference plate angle changing apparatus 31 includes the reference plate 15A rotatably supported about an axis 15X. By using the reference plate angle changing apparatus 31, the reference plate 15A can be moved in predetermined angular steps and the data of the reflected light can be acquired at each of the angular steps. In this way, the angle at which the highest signal value is read can be determined.

The gloss illumination angle changing apparatus 32 (FIG. 22) is configured to rotate the gloss illuminating apparatus 11 about the reading area 90a along a direction A on the X-Z plane. By rotating the gloss illuminating apparatus 11 about the reading area 90a along the direction A on the X-Z plane, the gloss illuminating apparatus 11 may be moved to positions within a range of 0° to 90°, for example, of the incident angle $\theta_1$ of the illuminating light 11a.

The imaging element angle changing apparatus 33 is configured to rotate the imaging element 13 about the reading area 90a along a direction B on the X-Z plane. By rotating the imaging element 13 about the reading area 90a along the direction B on the X-Z plane, the imaging element 13 may be moved to positions where the imaging element 13 can receive the specular reflected light within a range of 0° to 90°, for example, of the reflection angle $\theta_2$.

Figure 24:
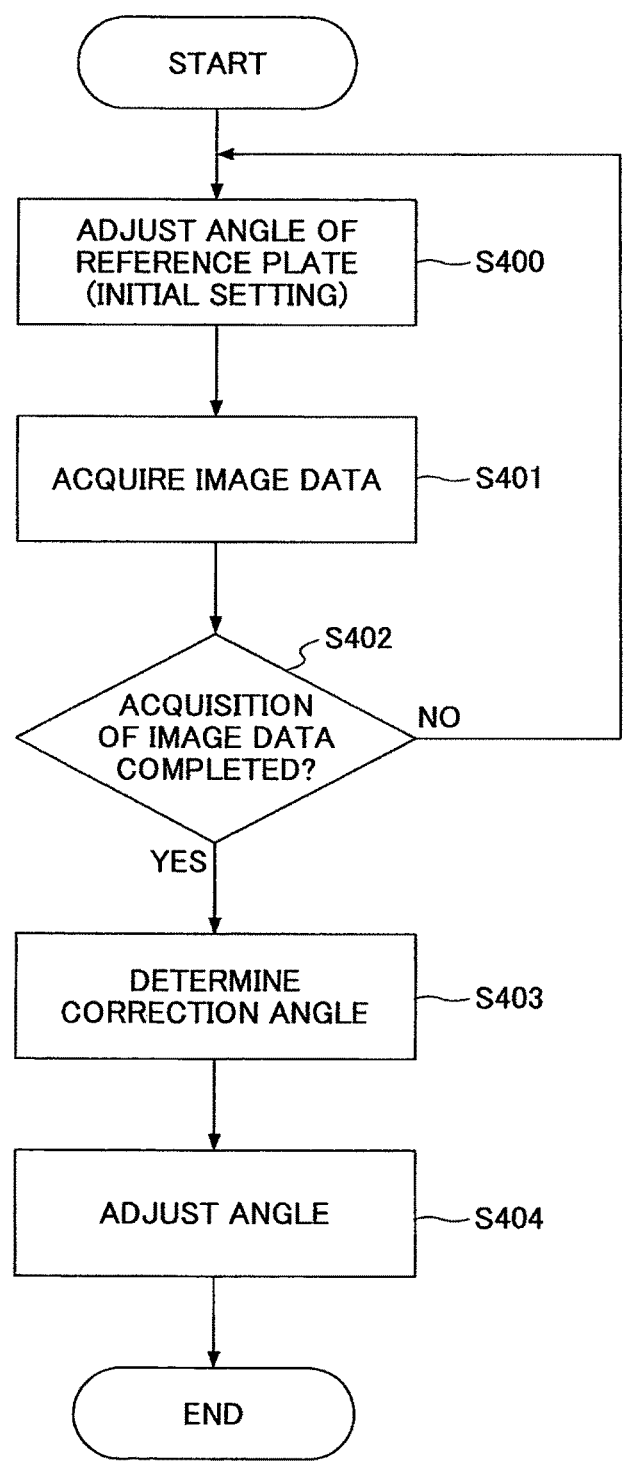
FIG. 24 is a flowchart of an angle adjusting process in the image inspecting apparatus.

In the following, a method of adjusting the incident angle $\theta_1$ and the reflection angle $\theta_2$ to be equal to each other in the image inspecting apparatus 30 is described. FIG. 24 is a flowchart of an example of the angle adjusting process in the image inspecting apparatus. In step S400, the reference plate 15A of the reference plate angle changing apparatus 31 is rotated about the axis 15X to adjust the angle of the reference plate 15A until an upper side of the reference plate 15A (on the side of the density illuminating apparatus 12 and the like) is aligned with the X direction in a side view. This position is determined to be the reference position (angle of ±0°). In FIG. 23, the direction of rotation of the reference plate 15A in which the incident angle $\theta_1$ is increased (i.e., the direction in which the incident angle $\theta_2$ is decreased) is indicated by the "+" sign, while the direction of rotation in which the incident angle $\theta_1$ is decreased (i.e., the direction in which the incident angle $\theta_2$ is increased) is indicated by the "−" sign.

In step S401, only the gloss illuminating apparatus 11 is turned on, and the reflected light reflected by the reference plate 15A is acquired by the imaging element 13 as image data Ga of the reference position (angle of ±0°). Then, the reference plate 15A of the reference plate angle changing apparatus 31 is rotated about the axis 15X to adjust the angle of the reference plate 15A until the upper side of the reference plate 15A (on the side of the density illuminating apparatus 12 and the like) is +1° with respect to the reference position in the side view. Then, only the gloss illuminating apparatus 11 is turned on, and the reflected light reflected by the reference plate 15A is acquired by the imaging element 13 as image data Gb of +1°. Similarly, the reference plate 15A of the reference plate angle changing apparatus 31 is rotated about the axis 15X to adjust the angle of the reference plate 15A until the upper side of the reference plate 15A (on the side of the density illuminating apparatus 12 and the like) is −1° with respect to the reference position in the side view. Then, only the gloss illuminating apparatus 11 is turned on, and the reflected light reflected by the reference plate 15A is acquired by the imaging element 13 as image data Gc of −1°.

In step S402, it is determined whether the image data has been acquired at all of the angles. When it is determined in step S402 that the acquisition of the image data is not completed ("No"), the same process is repeated from step S400. When it is determined in step S402 that the acquisition of the image data is completed ("Yes"), the process advances to step S403.

Figure 25A:
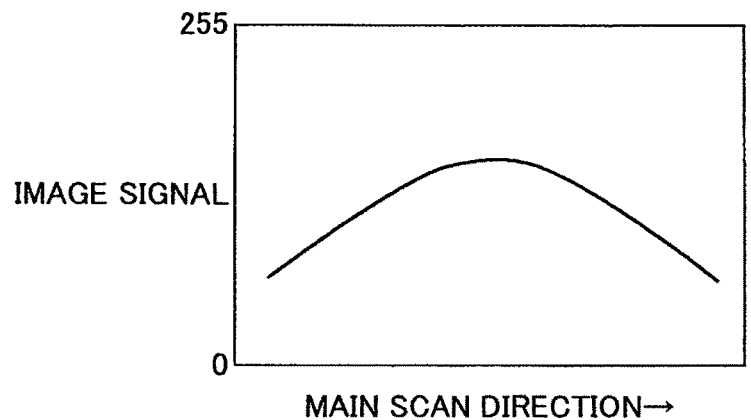
FIG. 25A illustrates an example of image data Ga (±0°) acquired in step S401.
Figure 25B:
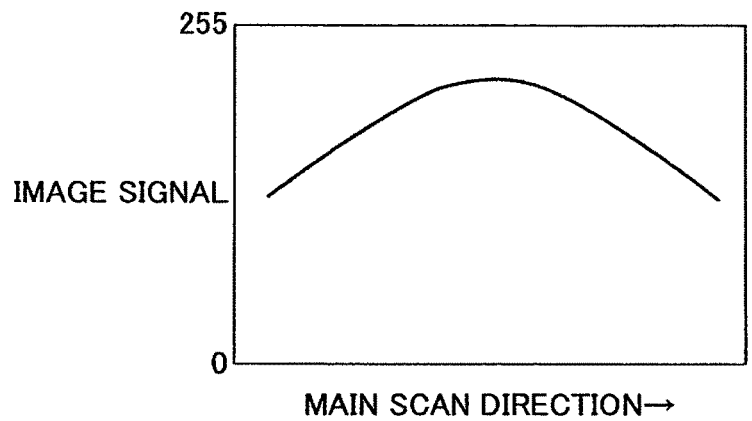
FIG. 25B illustrates an example of image data Gb (+1°) acquired in step S401.
Figure 25C:
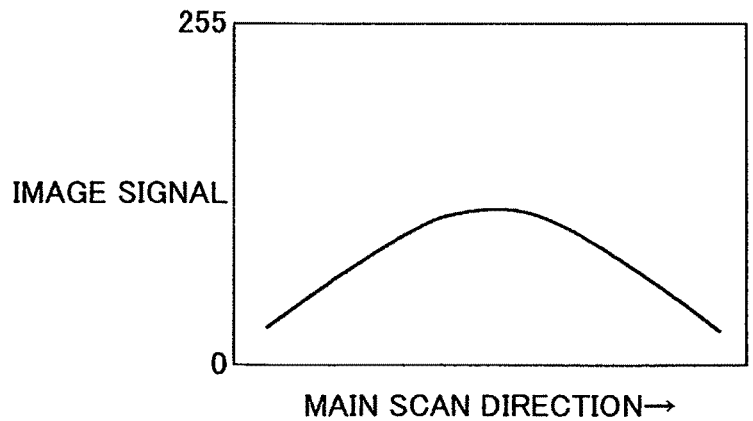
FIG. 25C illustrates an example of image data Gc (−1°) acquired in step S401.

In step S403, the image data Ga, Gb, and Gc read in step S401 are compared to determine the angle at which the image signal exhibits the largest value (i.e., the largest amount of light received) as a correction angle, as described below for example. FIG. 25A illustrates an example of the image data Ga (±0°) acquired in step S401. FIG. 25B illustrates an example of the image data Gb (+1°) acquired in step S401. FIG. 25C illustrates an example of the image data Gc (−1°) acquired in step S401. In this case, the image data Gb (+1°) indicates the largest image signal value. Thus, the angle of +1° is determined as the correction angle.

In step S404, the gloss illuminating apparatus 11 is rotated about the reading area 90a by the gloss illumination angle changing apparatus 32 along the direction A on the X-Z plane (see FIG. 22) until the gloss illuminating apparatus 11 is moved by +1° from the current position. In this case, the incident angle $\theta_1$ is increased by 1° with respect to the reference position from the current angle. Alternatively, instead of moving the gloss illuminating apparatus 11, the imaging element 13 may be rotated about the reading area 90a on the X-Z plane along the direction B by the imaging element angle changing apparatus 33 until the imaging element 13 is moved by −1° from the current position. In this case, the reflection angle $\theta_2$ is increased by 1° with respect to the reference position from the current angle.

In the example of FIG. 24, the angle of the reference plate 15A is changed at three angular steps (−1°, ±0°, and +1°). However, this is merely an example, and the angle may be set differently. While finer adjustment may be possible by making the angular steps finer or increasing the range of angles, the processing time increases proportionately.

In the example of FIGS. 22 and 23, the axis of rotation lies in the main scan direction (Y direction), the axis of rotation may lie in the sub-scan direction (X direction) or in both the main scan direction (Y direction) and the sub-scan direction (X direction). Preferably, not only the angle of the gloss illuminating apparatus 11 or the imaging element 13 but also the angle of a stage on which the measured object is mounted may be adjusted.

Thus, in accordance with the third embodiment, in addition to the effects provided by the first embodiment, the following effect can be obtained. Namely, it can be determined whether the incident angle and the reflection angle are equally set and, if not, the angle of the gloss illuminating apparatus or the imaging element can be adjusted such that the incident angle and the reflection angle are equal to each other.

Fourth Embodiment

Figure 26:
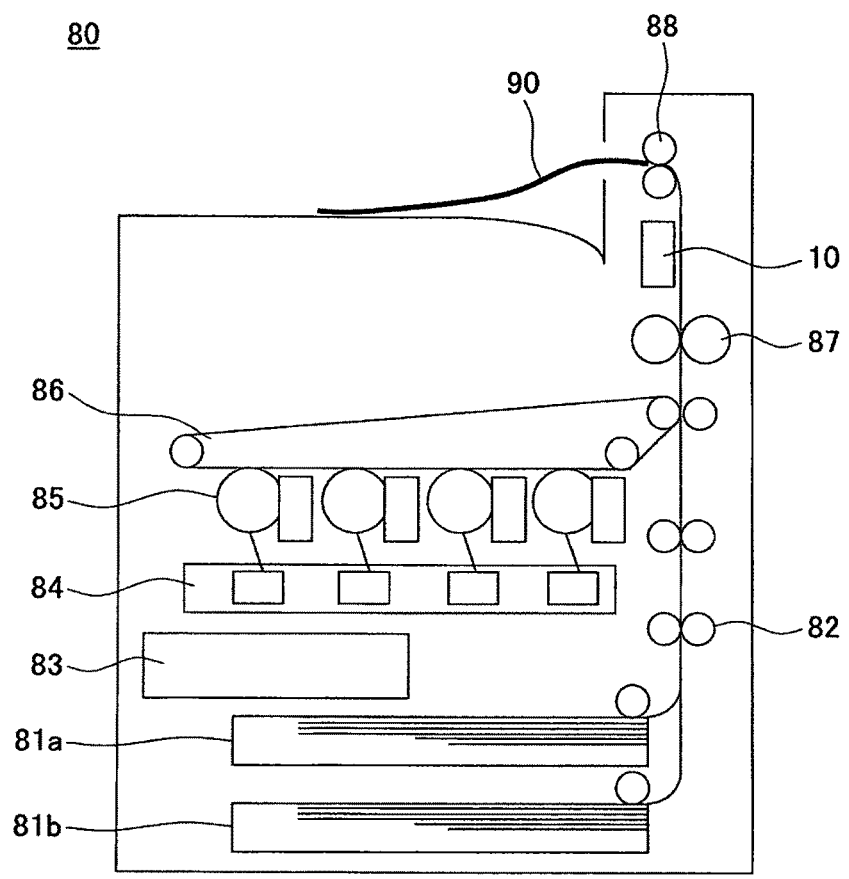
FIG. 26 illustrates an image forming apparatus according to a fourth embodiment of the present invention.

In accordance with the fourth embodiment, an image forming apparatus 80 includes the image inspecting apparatus 10 according to the first embodiment. FIG. 26 illustrates the image forming apparatus 80. The image forming apparatus 80 includes the image inspecting apparatus 10 according to the first embodiment, a sheet-feeding cassette 81a, a sheet-feeding cassette 81b, a sheet-feeding roller 82, a controller 83, a scanning optical system 84, a photosensitive body 85, an intermediate transfer body 86, a fusing roller 87, and a sheet-ejecting roller 88. Numeral 90 designates the image carrying medium (such as a sheet of paper).

In the image forming apparatus 80, the image carrying medium 90 is transported from the sheet-feeding cassette 81a or 81b by a guide unit (not illustrated) and the sheet-feeding roller 82. The photosensitive body 85 is exposed by the scanning optical system 84 and then developed with a coloring material. A developed image is transferred onto the intermediate transfer body 86 and then transferred from the intermediate transfer body 86 onto the image carrying medium 90. The image is then fused onto the image carrying medium 90 by the fusing roller 87. The image carrying medium 90 is thereafter ejected by the sheet-ejecting roller 88. The image inspecting apparatus 10 is installed at a stage following the fusing roller 87.

Thus, in accordance with the fourth embodiment, the image inspecting apparatus 10 according to the first embodiment is provided at a predetermined position in the image forming apparatus 80. Thus, the gloss distribution of the image carrying medium 90 on which the image is formed can be accurately inspected, and also the density distribution can be inspected. Further, by feeding the result of inspection of the gloss distribution or the density distribution back to the image forming process, a high-quality image can be formed on the image carrying medium 90. Preferably, the image inspecting apparatus 30 may be installed instead of the image inspecting apparatus 10.

Although this invention has been described in detail with reference to certain embodiments, variations and modifications exist within the scope and spirit of the invention as described and defined in the following claims.

The present application is based on Japanese Priority Application No. 2010-136432 filed Jun. 15, 2010, the entire contents of which are hereby incorporated by reference.

What is claimed is:

1. An image inspecting apparatus, comprising:
a first light illuminating unit configured to irradiate a measured object on which an image is formed with illuminating light from an inclined direction;
a second light illuminating unit configured to irradiate the measured object with illuminating light from a direction different from the inclined direction of the first light illuminating unit;
an imaging unit configured to receive reflected light of the illuminating light with which the measured object is irradiated by the first light illuminating unit, and reflected light of the illuminating light with which the measured object is irradiated by the second light illuminating unit;
a first reference plate having a mirror surface and configured to be irradiated instead of the measured object;
a second reference plate having a diffuse surface and configured to be irradiated instead of the measured object;
an image inspecting unit configured to inspect the image; and
a reference plate angle changing apparatus configured to change an angle of the mirror surface of the first reference plate with respect to a predetermined initial position, wherein
the image inspecting unit calculates a correcting coefficient based on a ratio of an amount of reflected light of illuminating light that is received by the imaging unit when the diffuse surface of the second reference plate is irradiated with the illuminating light from the first light illuminating unit to an amount of reflected light of illuminating light that is received by the imaging unit when the diffuse surface of the second reference plate is irradiated with the illuminating light from the second light illuminating unit,
the image inspecting unit inspects a gloss distribution of the image based on a value obtained by shading-correcting an amount of light obtained by subtracting an amount of reflected light of illuminating light that is received by the imaging unit when the measured object is irradiated with the illuminating light from the second light illuminating unit multiplied by the correcting coefficient, from an amount of reflected light of the illuminating light that is received by the imaging unit when the measured object is irradiated with the illuminating light from the first light illuminating unit, by using an amount of reflected light of illuminating light that is received by the imaging unit when the mirror surface of the first reference plate is irradiated with the illuminating light from the first light illuminating unit, and
the image inspecting unit acquires an amount of reflected light of the illuminating light with which the mirror surface of the first reference plate is irradiated by the first light illuminating unit for each of plural angles to which the angle of the mirror surface of the first reference plate is changed by the reference plate angle changing apparatus, and calculates an angular error between the first light illuminating unit and the imaging unit based on the acquired amount of reflected light.

2. The image inspecting apparatus according to claim 1, wherein the mirror surface is a mirror surface without any diffuse reflection and the diffuse surface reflects light with equal luminance in every direction.

3. The image inspecting apparatus according to claim 1, wherein the image inspecting unit determines whether a light-reflecting state of the mirror surface of the first reference plate is normal based on an amount of reflected light of illuminating light with which the mirror surface of the first reference plate is irradiated by the second light illuminating unit.

4. The image inspecting apparatus according to claim 1, further comprising a moving unit configured to move either the first light illuminating unit or the imaging unit in order to minimize the angular error.

5. The image inspecting apparatus according to claim 1, wherein the image inspecting unit inspects a density distribution of the image based on data obtained by shading-correcting an amount of reflected light of the illuminating light with which the measured object is irradiated by the second light illuminating unit, by using an amount of reflected light of illuminating light that is received by the imaging unit when the diffuse surface of the second reference plate is irradiated with the illuminating light from the second light illuminating unit.

6. An image inspecting method comprising:
a first step of irradiating a diffuse surface of a second reference plate with illuminating light from a first light illuminating unit in an inclined direction, and receiving reflected light of the illuminating light with an imaging unit;
a second step of irradiating the diffuse surface of the second reference plate with illuminating light from a second light illuminating unit in a direction different from the inclined direction of the first step, and receiving reflected light of the illuminating light with the imaging unit;
a third step of irradiating a mirror surface of a first reference plate with illuminating light from the first light illuminating unit in the inclined direction, and receiving reflected light of the illuminating light with the imaging unit;

a fourth step of calculating a correcting coefficient based on a ratio of an amount of the reflected light received in the first step to an amount of the reflected light received in the second step;

a fifth step of irradiating a measured object on which an image is formed with illuminating light from the first light illuminating unit in an inclined direction, and receiving reflected light of the illuminating light with the imaging unit;

a sixth step of irradiating the measured object with illuminating light from the second light illuminating unit in a direction different from the inclined direction of the fifth step, and receiving reflected light of the illuminating light with the imaging unit;

a seventh step of inspecting a gloss distribution of the image based on a value obtained by shading-correcting an amount of light obtained by subtracting a value obtained by multiplying an amount of reflected light of the illuminating light with which the measured object is irradiated in the sixth step with the correcting coefficient, from an amount of reflected light of the illuminating light with which the measured object is irradiated in the fifth step, by using an amount of the reflected light received in the third step;

an eight step of changing an angle of the mirror surface of the first reference plate with respect to a predetermined initial position;

a ninth step of acquiring an amount of reflected light of the illuminating light with which the mirror surface of the first reference plate is irradiated by the first light illuminating unit for each of plural angles to which the angle of the mirror surface of the first reference plate is changed by the eight step; and a tenth step of calculating an angular error between the first light illuminating unit and the imaging unit based on the acquired amount of reflected light.

7. The image inspecting method according to claim 6, wherein the mirror surface is a mirror surface without any diffuse reflection and the diffuse surface reflects light with equal luminance in every direction.

8. The image inspecting method according to claim 6, further comprising:

an eighth step of irradiating the mirror surface of the first reference plate with illuminating light from the second light illuminating unit in a direction different from the inclined direction of the first step, and receiving reflected light of the illuminating light with the imaging unit; and a ninth step of determining whether a light-reflecting state of the mirror surface of the first reference plate is normal based on an amount of the reflected light received in the seventh step.

9. The image inspecting method according to claim 6, further comprising:

a tenth step of acquiring an amount of reflected light of illuminating light with which the mirror surface of the first reference plate is irradiated by the first light illuminating unit with the imaging unit for each of plural angles to which an angle of the mirror surface of the first reference plate is changed by the reference plate angle changing apparatus with respect to a predetermined initial position; and an eleventh step of calculating an angular error between the first light illuminating unit and the imaging unit based on the amount of reflected light acquired in the tenth step.

10. The image inspecting method according to claim 9, further comprising a twelfth step of either moving the first light illuminating unit or the imaging unit in order to minimize the angular error.

11. The image inspecting method according to claim 6, further comprising a thirteenth step of inspecting a density distribution of the image based on data obtained by shading-correcting an amount of reflected light of the illuminating light with which the measured object is irradiated by the second light illuminating unit, by using an amount of reflected light of illuminating light that is received by the imaging unit when the diffuse surface of the second reference plate is irradiated with the illuminating light from the second light illuminating unit.

12. An image forming apparatus for forming an image on an image carrying medium, comprising the image inspecting apparatus according to claim 1, wherein the image inspecting apparatus is configured to inspect at least one of a gloss distribution and a density distribution of the image formed on the image carrying medium.

13. An image inspecting apparatus comprising:

a first light illuminating unit configured to irradiate a measured object on which an image is formed with light;

a second light illuminating unit configured to irradiate the measured object with light;

an imaging unit configured to receive reflected light of the light with which the measured object is irradiated by the first light illuminating unit and the second light illuminating unit;

a first and a second reference plate having a mirror surface and a diffuse surface, respectively;

a reference plate angle changing apparatus configured to change an angle of the mirror surface of the first reference plate with respect to a predetermined initial position, and an image inspecting unit configured to inspect a gloss distribution of the image based on the amount of light received by the imaging unit and a correcting coefficient, wherein the image inspecting unit acquires an amount of reflected light of the light with which the mirror surface of the first reference plate is irradiated by the first light illuminating unit for each of plural angles to which the angle of the mirror surface of the first reference plate is changed by the reference plate angle changing apparatus, and calculates an angular error between the first light illuminating unit and the imaging unit based on the acquired amount of reflected light.

* * * * *